United States Patent [19]

Hellgren et al.

[11] Patent Number: 4,695,457

[45] Date of Patent: Sep. 22, 1987

[54] ENZYME COMPOSITION ACTING AS A DIGESTION PROMOTER ON VARIOUS LEVELS IN THE ALIMENTARY TRACT, AND A METHOD FOR FACILITATING DIGESTION

[75] Inventors: Lars G. I. Hellgren, Västra Frölunda, Sweden; Viggo Mohr, Trondheim, Norway; Jan G. Vincent, Stockholm, Sweden

[73] Assignee: Pharmacia AB, Uppsala, Sweden

[21] Appl. No.: 829,642

[22] PCT Filed: Apr. 24, 1985

[86] PCT No.: PCT/SE85/00187

§ 371 Date: Dec. 3, 1985

§ 102(e) Date: Dec. 3, 1985

[87] PCT Pub. No.: WO85/04809

PCT Pub. Date: Nov. 7, 1985

[30] Foreign Application Priority Data

Apr. 24, 1984 [SE] Sweden ............................ 8402238

[51] Int. Cl.⁴ .......................................... A61K 37/48
[52] U.S. Cl. ................................................... 424/94
[58] Field of Search ......................................... 424/94

[56] References Cited

U.S. PATENT DOCUMENTS

| 3,313,705 | 4/1967 | Constant et al. | 424/110 |
|---|---|---|---|
| 3,357,894 | 12/1967 | Uriel et al. | 435/229 |
| 3,803,304 | 4/1974 | Antonides et al. | 424/94 |
| 3,925,158 | 12/1975 | Betzing et al. | 435/226 |
| 3,956,483 | 5/1976 | Lewis | 424/94 |
| 4,088,539 | 5/1978 | Muller | 435/226 |

FOREIGN PATENT DOCUMENTS

| 1015566 | 10/1952 | France . |
|---|---|---|
| 01715 | 5/1984 | PCT Int'l Appl. . |
| 140568 | 6/1953 | Sweden . |
| 377128 | 7/1932 | United Kingdom . |
| 1561613 | 2/1980 | United Kingdom . |

OTHER PUBLICATIONS

Chen et al., J. Food Biochem., 2:349–366, 1978.
Gildberg Thesis, Jun. 1982.
Rote Liste 1977/78, No. 59249 cb, 59256 cb and 59260 cb.
Chem. Abstr. 89:55330a, 1978; 90:35434e, 1972.
Chem Ab. 92:116420r, 1980; 92116421s, 1980; 98:13723m, 1983.
Patent Abst. of Japan 58-162524, 9/27/83.

Primary Examiner—Johnnie R. Brown
Assistant Examiner—John W. Rollins
Attorney, Agent, or Firm—Fred Philpitt

[57] ABSTRACT

A pharmaceutical composition containing an effective amount of an enzyme preparation which is capable of promoting decomposition of food containing meat and/or adipose tissue and is produced from aquatic animals selected from the group consisting of animals of the order Euphausiaceae and animals of the genus Mallotus, said composition being useful as a digestion promoter in gastrointestinal fluids.

The invention comprises also a method for promoting degradation of food in gastrointestinal fluids by means of adding or administering said pharmaceutical composition.

6 Claims, No Drawings

ENZYME COMPOSITION ACTING AS A DIGESTION PROMOTER ON VARIOUS LEVELS IN THE ALIMENTARY TRACT, AND A METHOD FOR FACILITATING DIGESTION

FIELD OF THE INVENTION

The invention is concerned with an enzyme composition promoting digestion in the fluids present within the gastrointestinal tract. In particular, the invention relates to a pharmaceutical enzyme composition for the in vivo treatment of inadequate digestion in terrestrial mammals, especially man; in other words, the composition is to be used as a digestion promoter acting in the gastrointestinal tract. The invention is also concerned with a method for such a treatment. The composition contains an enzyme preparation derived from an aquatic animal of the order Euphausiaceae or of the genus Mallotus.

In the present specification and claims, the term "enzyme" refers to an active enzyme unless otherwise stated.

PRIOR ART

Digestion of ingested food starts in the mouth cavity and then goes on as the food passes through the stomach, the tract of the small intestine (duodenum, jejunum, ileum) and the colon. During this digestive process different enzymes act on different types of substrates in different regions (The Mitchell Beazley Atlas of the Body and Mind, 1976).

Inadequate digestion may be caused by various kinds of disturbances in the gastrointestinal tract. Examples of such disturbances are:

If the food is not crunched and kneaded sufficiently well in the mouth cavity and consequently the ptyalin of the saliva fails to mix efficiently with the carbohydrates, then the normal degradation of complex sugars to maltose will not proceed to a satisfactory degree.

In the cases of patients suffering from achlorhydria or hypochlorhydria in the stomach the conversion of proteins to acidic albumoses and peptones is impaired, thus rendering the digestive process incomplete. The same applies in case of inadequate pepsin excretion from the stomach wall.

If the bile from the gall bladder does not reach the lipids present in the duodenum this will result in an incomplete fat emulsification, with concomitant thwarting of an appropriate enzymatic degradation of the lipids.

The pancreatic gland may have undergone morbid changes preventing it from excreting a sufficient amount of enzymes for a fully satisfactory digestion of the lipids, proteins and carbohydrates. For example, the pancreas may have been excised because of a cancer; or the patient may suffer from pancreatic dysfunction due to a chronic pancreatitis that has been initiated by alcoholism; other examples are pancreatic fibrosis; hyperparathyroidism; gallstones; congenital pancreatic dysfunction.

If in the case of an individual that has undergone stomach surgery the food is caused to pass through the duodenum very quickly this may have the effect that the pancreas is not stimulated to a sufficient extent.

If due to shunt operations of the Bilroth II type the food goes directly from the stomach to the distal portions of the small intestine then again the pancreas is not stimulated to a sufficient extent and enzyme production becomes too low for an adequate digestion to occur.

Insufficient enzyme excretion in the lower portion of the small intestine (in the jejunum or ileum) may result in deficient final decomposition of e.g. proteins.

In cases where the bacterial flora of the colon has been severely reduced because of for instance oral administration of broad spectrum antibiotics the digestive process in the colon may be impaired so much as to become insufficient. This same condition sometimes arises also when food passes too quickly through this portion of the alimentary tract due to functional or organic causes (nervousness, colitis of various types, tumors, resection of the colon).

There exist at present numerous pharmaceutical enzyme compositions which are to assist the digestive process in cases of pancreatic failure or insufficiency; that is, these compositions are to enhance digestion in the duodenum. Pancreatin is an example of such a drug (GB No. 1561613). Enzymes derived from fish intestines and from other aquatic animals have likewise been described as digestion promoters (FR No. 1015566). Commercially available products are for example Combizym ®, Combizym ® comp., Festal ®, Luizym ®, all of them containing an extract from *Aspergillus oryzae*. All of these except Luizym ®, contain pancreatin; two of these, viz. Combizym ® comp and Festal ®, contain bile acids, Pankreon ®, Pankreon ® forte and Pankreon ® comp are pancreatin-based compositions one of which (Pankreon ® comp) contains additionally bile acids; these added bile acids act as emulsifiers which increase the effect of the lipases.

The problems inherent in prior art enzyme drugs are due to the fact that these drugs are unstable in the acidic gastric environment and are quite inefficient in degrading normal food ingredients. For this reason many of the compositions employed heretofore have been coated with a material resistant to gastric juice so that the enzymes are not released before they reach the duodenum. Inactivation may be avoided to some extent if the drugs are ingested together with food or are ingested in the form of compositions containing certain neutralizing salts; but more often than not such combinations have proved to be unsatisfactory. Furthermore, some of the compositions used heretofore have been found to adversely affect the gastric mucosa.

Aquatic animals belonging to the order of Euphausiaceae such as for example krill (*Euphausia superba*) contain a variety of enzymes. Among these may be mentioned proteinases (proteolytic enzymes) some of which have acidic pH optima while others have neutral to alkaline pH optima; peptidases (exo and endopeptidases); lipases; phospholipases; amylases and other carbohydrate-splitting enzymes; phosphatases; nucleases; nucleotidases; and esterases (T. E. Ellingsen, "Biokjemiske studier over antarktisk krill" dr. ing. thesis, Institutt for Teknisk Biokjemi, Norges Tekniske Höjskole, Trondheim, Norway, 1982). The proteolytic (trypsin-like) activity found in aqueous extracts of krill has been described by C.-S. Chen et al. in J. Food Biochem. 2 (1978), p. 349-66. Various protease activities contained in aqueous extracts from aquatic animals of the genus Mallotus, especially *Mallotus villosus*, have also been described (A. Gildberg "Autolysis of Fish Tissue - General Aspects", Thesis, Institute of Fisheries, University of Tromsö, Norway, 1982).

THE INVENTION

Objects of the invention are to provide improvements in enzyme-based promoters of in vivo digestion in various localities and on various levels, and more specifically to provide a digestion promoter drug which is active in the juices of the gastrointestinal tract.

The invention employs an effective amount of an enzyme preparation derived from an aquatic animal selected from the group consisting of animals of the order Euphausiaceae and animals of the genus Mallotus. The term "effective amount" means an amount capable of promoting digestion and/or decomposition of normal food which contains meat and natural fat (=adipose tissue) i.e. food containing proteins and lipids.

The enzyme composition according to the present invention contains proteinase activity from the aquatic animals which constitute the starting material for the composition. The composition may contain also lipase activity and/or amylase activity in admixture with various additives such as e.g. bile and various preparations of fluids from the duodenum and stomach. The lipase and/or amylase activities may derive from these same aquatic animals or from other sources.

The compositions will perform as potential aids in all kinds of metabolic processes in vivo, within the entire digestive system from the oral cavity down to the anus. In other words, the compositions are useful for treating such disturbances or disorders in the digestive process as have been described in the opening portions of this specification.

Enzyme mixtures from the aforesaid animals may be obtained in high yields and in a simple manner. Useful sources for the enzyme formulation are animals of the order Euphausiaceae, for instance antarctic krill (*Euphausia superba*), *Euphausia crystallorophias*, and other krill species including e.g. *Meganyctiphanes norvegica*, *Tysanoessa inermis* and other related species. Within the Mallotus genus a particularly important species is the marine fish *Mallotus villosus* (capelin).

The most important enzyme activities in the context of the present invention originate from the alimentary tract of the animals. Various different forms of mixtures of enzyme activities may be obtained, depending on the manufacturing method employed.

The enzymes are prepared from the animals by means of well-known methods. Fresh or fresh-frozen animals are homogenized and thus extracted with an aqueous medium (e.g. water). The resultant extract may be lyophilized and stored. The extract may be purified further by e.g. extraction with a lipid-dissolving solvent for lipid removal.

If then still further purification is necessary this may be effected by gel filtration, ultrafiltration or membrane filtration, it being possible by means of these procedures to remove low molecular compounds containing for instance fluorine (krill is known to be rich in fluorine). Other available purification steps to which recourse may be had are ion exchange chromatography and affinity chromatography. Extraction and homogenization should be performed in the cold, below or close to +5° C.

The enzyme preparations obtained by aqueous extraction may be employed as such directly, or after further purification if required. In some cases it is advantageous to lyophilize a preparation from which lipids have been removed by extraction; the powder thus obtained can be stored for a long time.

According to the invention the enzymes employed and originating from the aforesaid type of animals have a molecular weight within the range of from 15,000 to 200,000 daltons. In particular, the proteinases have molecular weights ranging from 15,000 to 80,000 daltons, for instance from 20,000 to about 40,000 daltons (e.g. trypsin-like enzymes and carboxypeptidase A and B). These ranges apply to enzymes in a non-aggregated form such as obtained upon aqueous extraction of the homogenized animals. Preferred proteinases are soluble in water, such as for instance those that remain in the aqueous phase after the aforesaid extractions According to the invention a mixture of hydrolytic enzymes are used, e.g. endopeptidases showing trypsin activity in combination with exopeptidases such as aminopeptidases and carboxypeptidase A and B.

Digestion promoters used heretofore have been employed in various types of drug formulations. Those same types are useful also in the case of the present invention: The compositions of the present invention may take the form of a paste, cream, gel, oil, solution, granulated material; or capsule, pill, tablet, pellet, any of these latter if desired in a sustained-release form; etc. The most important medical formulations are: Tablets, especially coated tablets;. capsules, especially capsules of a type that are resistant to gastric juice; and pellets, especially microencapsulated pellets. However, within the scope of the present invention formulations that are not coated for gastric juice resistance may occasionally be of particularly great value, if this corresponds to the needs of an individual to be treated.

Different types of formulations and/or different types of coatings may be utilized for programming the compositions to release their activity in very specifically predetermined places within the gastrointestinal tract. The compositions may thus be coated with a layer providing resistance to gastric juice, and/or they may be formulated so as to gradually release their activity during a prolonged period of time. For practical reasons oral drug formulations are preferred.

In cases of pancreatic dysfunction—the most important indication for digestion promoters—the compositions employed are preferably formulated so as to be resistant to gastric juice. This type of formulations will provide optimum enzyme activity in the right place, i.e. in the duodenum or further down in the intestinal tract.

With this type of preferred formulations the enzymes are released mainly after the compositions have passed through the stomach; their release thus takes place in the intestines, preferably in the duodenum. In other words, the enzyme should be released at pH higher than 6.5.

Techniques for manufacturing capsules, tablets, pellets etc. which are resistant to gastric juice and have predetermined release properties in intestinal juice have been known per se, cp. "The Theory and Practice of Industrial Pharmacy" Lachman L., Lieberman H. and Klanig J. L., 2nd Edition, Lea Febiger, Philadelphia, USA (1976), pp. 321–465.

A formulation that is to be resistant to gastric juice should be of a quality such as to remain unaffected by simulated gastric juice during four hours at 37° C. and then should not release its active components before another 30 minutes have elapsed in simulated intestinal juice (US Pharmacopoea XX, p. 1105 and the 3rd supplement thereof pp. 310–311).

Capsules of various sizes are commercially available. They usually consist of gelatin or some other material which is innocuous to the gastrointestinal tract. Filled capsules and compressed tablets are rendered resistant to gastric juice by being coated with an acid-resistant film (enteric coating). Furthermore, it may be noted that dissolution rates are determined also by the material of the capsule wall and by the carrier material employed. Thus for instance, it is possible to choose certain types of gelatin which are dissolved at the pH of the intestine but remain undissolved at the pH of the stomach. In such a case requirements are less strict as regards enteric coatings.

The enteric film coating operation is carried out in that a film coating material which is resistant to gastric juice is dissolved in a volatile solvent and the solution is then sprayed onto filled capsules, tablets, pellets or the like.

Such film coating materials are commercially available from numerous sources. They may consist of non-toxic cellulose ethers or synthetic polymers.

For preparing the compositions, an enzyme preparation obtained from the aforesaid aquatic animals may be combined with various known per se carriers/additives which are physiologically acceptable. Suitable carriers are conventional constituents of tablets, capsules, granulates etc; organic and inorganic materials such as silicone oils or other substances and mixtures bestowing desired properties on the composition. It is even possible, within the general concept of this invention, to employ aqueous solutions formed by combining the enzyme preparation with distilled water or physiological saline. Among additives of an active type may be mentioned bile salts and bile acids as aforesaid, as well as varous preparations from gastric juice or intestinal juice. Coloring substances, flavoring agents, preservatives, emulsifiers, salts of mildly alkaline reaction etc. may also be added. The additives and carriers employed should be chosen such that they will not have any significant side effects on the intended promotion of the digestive processes.

The dosage unit form of the composition may be chosen from among a variety of such forms. In the case of tablets, capsules etc. the weight of each dosage unit is usually less than 0.5 g, these dosage units being intended for administration in an amount of say 1 to 2 tablets (to be ingested during or after meals) e.g. 2 to 3 times per day.

The final composition according to the present invention will normally contain protein from the aforesaid aquatic animals in an amount of from 0.0001 to 100% (w/w), e.g. from 0.001 to 90% (w/w). The exact amount will depend on the particular type of composition employed and on the specific enzyme activity per mg of animal protein.

As regards the proteinase activity in the final composition, this will often be within a range of from 0.1 to 0.0001 enzyme units per mg; but in some cases other activity per mg ranges may be obtained, depending on the purity of the enzyme preparation. The enzyme units as stated above are in $\mu$mol tyrosine equivalents per min., with casein as the substrate.

Various embodiments of the invention will be illustrated below in a number of examples and will also be apparent from the appended claims. In some of the example fluids from the gastrointestinal tract have been employed These have been collected from healthy individuals.

In the examples the effect of the enzymatic digestion on the substrate is expressed as % of the initial substrate weight. In the course of each experiment the weight of the substrate decreases due to enzymatic digestion and increases due to water adsorption which in turn depends on the degree of digestion. Positive (+) values indicate liquefaction (increase in tissue weight) whereas negative (−) values indicate a digestive effect (decrease in tissue weight).

The incubation temperature was 37° C. The substrates chosen were meat (proteinaceous tissue) and fat (adipose tissue).

| Designation | Type of effect | Degradation range |
|---|---|---|
| − − − − | decrease in weight | 76–100% of the tissue |
| − − − | decrease in weight | 51–75% of the tissue |
| − − | decrease in weight | 26–50% of the tissue |
| − | decrease in weight | 1–25% of the tissue |
| 0 | status quo | 0 |
| + | increase in weight | 1–25% of the tissue |
| + + | increase in weight | 26–50% of the tissue |
| + + + | increase in weight | 51–75% of the tissue |
| + + + + | increase in weight | 76–100% of the tissue |

EXAMPLE 1

A. Preparation of Krill Extract

Krill (*Euphausia superba*) caught during the antarctic summer season and immediately frozen, and then stored for about two years at −80° C., is introduced in to a room of +5° C. temperature. When the krill has almost thawed 25 g thereof are mixed with 50 ml of deionized water of 0° C. The mixture is homogenized and centrifuged in the cold (about 0° C.) for half an hour at 12,500 g. The red upper phase is recovered by decantation. The sediment is then resuspended in 50 ml of deionized water and centrifuged as above. The new upper phase is again decanted and pooled with the upper phase from the first extraction.

For the removal of lipids from the extract 20 ml of $CCl_4$ is added to the pooled upper phase which is then homogenized in the cold (0° C.). The mixture is centrifuged in the cold at 2500 g for 15 minutes. The aqueous phase is removed and extracted once more with $CCl_4$ and then centrifuged as above. Finally the aqueous phase is lyophilized and employed as described in Sec. 1B where it is referred to as "the aqueous extract".

B. Additional Purification by Means of Gel Chromatography 20 ml of the aqueous extract from A is chromatographed on Sephadex ® G-100 (dextran crosslinked with epichlorohydrin, Pharmacia Fine Chemicals AB, Uppsala, Sweden) in a column of 3.1 cm diameter and 69 cm in height. The column is equilibrated and eluted (30 ml per hour) with Tris-HCl buffer (0.05 m, pH 7.5) at +5° C. Fractions are collected. The elution procedure is monitored spectrophotometrically by measurement of the UV adsorption at 280 nm and determination of the proteolytic activities in the individual fractions separately. The enzymatically active fractions are pooled and dialyzed against deionized water. Finally the pooled fractions are lyophilized and employed in accordance with the present invention. Proteolytic activities in the fractions and in the lyophilized product are determined with the aid of hemoglobin and/or casein as the substrates (Rick, W. I. "Methods of Enzymatic Analysis" Ed. Bergmeyer, H. U., Vol. 2, pp. 1013–1023 (1974), Academic Press, New York, USA). By means of this gel chromatography procedure enzyme activity is recovered mainly from fractions corresponding to molecular weights of 20,000 to 40,000 daltons. By the method given above no significant proteolytic activity could be detected in the fractions corresponding to molecular weights lower than 15,000 daltons or higher than 80,000 daltons.

C. Preparation of Crude Extract From Krill 60 g of krill, *Euphausia superba,* is homogenized with 100 ml of water. The krill material and the method are the same as described in Example 1A. After the homogenization the mixture is centrifuged in the cold (about 0° C.) for half an hour at 12,500 g. The upper phase is decanted, frozen and then employed in Example 13.

EXAMPLE 2

Preparation of crude extract from *Mallotus villosus*

Capelin (*Mallotus villosus*) was caught in the sea off the coast of Finnmark (Norway) during the month of September. It was frozen and stored for one year at −20° C. The frozen capelin was introduced into a room of +5° C. temperature. After 24 hours the intestines, including the digestive tract, were removed from the capelin which by then had partially thawed. 60 g of the intestines were mixed with 100 ml of deionized water and homogenized at 0° C. The mixture was then centrifuged for half an hour at 12,500 g. The upper phase, somewhat turbid, was decanted and frozen in order to then be employed in Example 13.

EXAMPLE 3

Detection of Different Enzyme Activities

The purified krill preparation used in the examples 4–12 as an aid for digestive processes contains endopeptidase and exopeptidase activities represented by trypsin and carboxypeptidase A and B, respectively. Preliminary measurements indicate the presence of carbohydrate-splitting enzymes and phosphatases. A crude aqueous krill extract contains in addition to the above-mentioned enzymes also an aminopeptidase (Mw=120,000–150,000 dalton).

The protease activities (trypsin, carboxypeptidase A and B) were determined for the purified extract according to the methods described in the reference list (1–3). The total proteolytic activity was determined using denatured casein as a substrate (1,4). The protein content was analysed using the Folin Ciocalteu phenol reagent according to the Lowry method (5).

The enzymatic activities obtained were calculated and expressed as specific activity in units per mg protein (Table 1).

References

1. Rich, W.: Methods of enzymatic analysis Edited by Bergmeyer, H. U., 2nd edition, Academic Press, New York 1974, Vol. 2, p. 1013.
2. Folk, J. E. and Schirmer, E. W.; J. Biol. Chem. 238(1963) 3884.
3. Folk, J. E., Piez, K. A., Carrol, W. R. and Gladner, J.; J. Biol. Chem. 235(1960) 2272.
4. Kunitz, M.; J. Gen. Physiol. 30(1947) 291.
5. Lowry, H., Rosenbrough, N. J., Farr, A. L. and Randall, R. J.; J. Biol. Chem. 193(1951) 265.

TABLE 1

| | |
|---|---|
| Proteolytic activity | 4.28 units*/mg protein |
| Trypsin | 12.70 units*/mg protein |
| Carboxypeptidase A | 3.86 units*/mg protein |
| Carboxypeptidase B | 2.11 units*/mg protein |

*Definition of the unit

Proteolytic Activity

Casein as substrate.

1 unit causes the formation of 1 μmole tyrosine equivalents per ml within 20 minutes.

Trypsin p-Toluenesulfonyl-L-arginine methyl ester (TAME) as substrate. 1 unit causes the hydrolysis of 1 μmole substrate per minute.

Carboxypeptidase A

Hippuryl-L-phenylalanine as substrate.

1 unit causes the hydrolysis of 1 μmole substrate per minute.

Carboxypeptidase B

Hippuryl-L-arginine as substrate.

1 unit causes the hydrolysis of 1 μmole substrate per minute.

EXAMPLE 4

Effect of Krill Enzymes on Meat Digestion

Frozen meat (raw) was cut into small pieces, then was thawed and divided into aliquot portions. Each aliquot (0.1–0.2 g) was weighed and added to 1 ml of freshly prepared enzyme solution (test solution) containing either lyophilized krill enzyme preparation (0.01 or 0.001 g/ml, from Example 1B) or Pankreon ® (0.01 or 0.001 g/ml, Kali-Chemie GmbH, Hannover, Germany). The test solutions were prepared by dissolving the enzyme preparations in distilled water. The pieces of meat, pre-weighed, were introduced into the test solutions and incubated for varying periods of time as indicated in Table 2. After this exposure the meat was placed on a filter paper for 15 seconds whereupon it was weighed. Ocular inspection showed that the krill enzymes had transformed the meat in a manner substantially different from the effect of Pankreon ®. This experiment also included controls in the form of meat pieces incubated in water under identical experimental conditions.

TABLE 2

| Enzyme composition | Conc. g/ml | Decrease in weight (−) ("digestive effect") or increase in weight (+) ("liquefaction effect") after 2 to 14 hours, expressed as % of the initial values | | | | | | |
|---|---|---|---|---|---|---|---|---|
| | | 2 | 4 | 6 | 8 | 10 | 12 | 14 |
| Pankreon ® | 0.01 | +(+) | + | + | + | (−) | − | − |
| | 0.001 | + | + | + | + | + | + | (+) |
| Krill | 0.01 | + | (+) | (−) | − | −− | −−− | −−−−(−) |
| | 0.001 | + | + | + | (+) | (−) | − | − |
| Control | | ++ | ++ | ++ | ++ | ++ | +(+) | +(+) |

TABLE 2-continued

| Enzyme composition | Conc. g/ml | Decrease in weight (−) ("digestive effect") or increase in weight (+) ("liquefaction effect") after 2 to 14 hours, expressed as % of the initial values | | | | | | |
|---|---|---|---|---|---|---|---|---|
| | | 2 | 4 | 6 | 8 | 10 | 12 | 14 |
| (water) | | | | | | | | |

These results Indicate that the krill enzyme preparation was a more potent meat digester than Pankreon ®.

EXAMPLE 5

Effect of Krill Enzymes on Meat Digestion in the Presence of Gastric Juice

The procedure was the same as in Example 4 except that the enzyme preparation was dissolved in gastric juice rather than in water.

TABLE 3

| Enzyme composition | Conc. g/ml | Decrease in weight (−) ("digestive effect") or increase in weight (+) ("liquefaction effect") after 2 to 14 hours, expressed as % of the initial values | | | | | | |
|---|---|---|---|---|---|---|---|---|
| | | 2 | 4 | 6 | 8 | 10 | 12 | 14 |
| Krill | 0.01 | + | (+) | − | −− | −−− | −−−− | −−−− |
| | 0.001 | ++ | + | + | − | −(−) | −− | −−−(−) |
| Control (gastric juice) | | ++ | +(+) | + | (−) | − | −(−) | −− |

The results of Examples 4 and 5 indicate that freshly collected gastric juice potentiates the effect exerted by the krill enzymes. This synergistic effect persists during the entire test period (14 hours) showing that the krill enzymes are stable under these conditions. Preliminary results obtained with Pankreon ® are consistent with the information of its producer saying that its effect in gastric juice is poor.

EXAMPLE 6

Effect of Krill Enzymes on Protein Digestion in the Presence of a Mixture of Juices from the Stomach and the Duodenum The prodedure was the same as in Example 4 except that the enzyme composition was dissolved in a freshly prepared mixture of juices from the stomach and duodenum, rather than in water.

TABLE 4

| Enzyme composition | Conc. g/ml | Decrease in weight (−) ("digestive effect") or increase in weight (+) ("liquefaction effect") after 2 to 14 hours, expressed as % of the initial values | | | | | | |
|---|---|---|---|---|---|---|---|---|
| | | 2 | 4 | 6 | 8 | 10 | 12 | 14 |
| Krill | 0.01 | +(+) | (−) | − | −− | −−− | −−−− | −−−− |
| | 0.001 | ++ | + | (−) | −(−) | −− | −− | −−− |
| Control (gastric and duodenal juice) | | ++ | ++ | + | (+) | −(−) | −− | −− |

These results and the conclusions to be drawn therefrom are analogous to those of Example 5.

EXAMPLE 7

Effect of Krill Enzymes on the Digestion of Adipose Tissue

The procedure was the same as in Example 4 except that the meat was replaced by natural fat (raw, adipose tissue) as the substrate for the enzymes.

TABLE 5

| Enzyme composition | Conc. g/ml | Decrease in weight (−) ("digestive effect") or increase in weight (+) ("liquefaction effect") after 2 to 14 hours, expressed as % of the initial values | | | | | | |
|---|---|---|---|---|---|---|---|---|
| | | 2 | 4 | 6 | 8 | 10 | 12 | 14 |
| Krill | 0.01 | + | + | (−) | − | −(−) | −− | −− |
| | 0.001 | + | + | + | + | (+) | − | − |
| Pankreon ® | 0.01 | + | + | + | + | + | + | + |
| | 0.001 | + | + | + | + | + | + | + |
| Control (water) | | + | + | + | + | + | + | + |

These results show that krill enzymes are highly efficient in decomposing adipose tissue.

EXAMPLE 8

Effect of Krill Enzymes on the Digestion of Adipose Tissue in the Presence of Gastric Juice The procedure was the same as in Example 7 except that the enzyme preparations were dissolved in gastric juice rather than in water.

TABLE 6

| Enzyme composition | Conc. g/ml | Decrease in weight (−) ("digestive effect") or increase in weight (+) ("liquefaction effect") after 2 to 14 hours, expressed as % of the initial values | | | | | | |
|---|---|---|---|---|---|---|---|---|
| | | 2 | 4 | 6 | 8 | 10 | 12 | 14 |
| Krill | 0.01 | − | −− | −−−(−) | −−−− | −−−− | −−−− | −−−− |

TABLE 6-continued

| | | Decrease in weight (−) ("digestive effect") or increase in weight (+) ("liquefaction effect") after 2 to 14 hours, expressed as % of the initial values | | | | | | |
|---|---|---|---|---|---|---|---|---|
| Enzyme composition | Conc. g/ml | 2 | 4 | 6 | 8 | 10 | 12 | 14 |
| | 0.001 | − | − − | − − − | − − − | − − − − | − − − − | − − − − |
| Control (gastric juice) | | (−) | − | − − | − − − | − − − − | − − − − | − − − − |

The results of Examples 7 and 8 show that freshly collected gastric juice potentiates the effect exerted by the krill enzymes. This synergistic effect persists during the entire test period showing that the krill enzymes are stable under these conditions. Preliminary results obtained with Pankreon ® are similar to the results reported in Example 5.

EXAMPLE 9

Effect of Krill Enzymes on the Digestion of Adipose Tissue in the Presence of Gastric/Duodenal Juice The procedure was the same as in Example 7 except that the enzyme preparations were dissolved in a freshly prepared mixture of gastric and duodenal juices rather than in water.

TABLE 7

| | | Effect on fat: Decrease in weight (−) ("digestive effect") or increase in weight (+) ("liquefaction effect") after 2 to 14 hours, expressed as % of the initial values | | | | | | |
|---|---|---|---|---|---|---|---|---|
| Enzyme composition | Conc. g/ml | 2 | 4 | 6 | 8 | 10 | 12 | 14 |
| Krill | 0.01 | − | − − | − − − − | − − − − | − − − − | − − − − | − − − − |
| | 0.001 | − | − − | − − − | − − − | − − − − | − − − − | − − − − |
| Control (gastric/duodenal juice) | | − | − − | − − | − − − | − − − − | − − − − | − − − − |

These results and the conclusions to be drawn therefrom are analogous to those of Example 8. Preliminary results with Pankreon ® did not indicate any substantial degradation as compared to the control.

EXAMPLE 10

Effect of Krill Enzymes on the Digestion of Meat in the Presence of Saliva

The procedure was the same as in Example 4 except that the enzyme preparations were dissolved in fresh saliva rather than in water.

TABLE 8

| | | Effect on protein: Decrease in weight (−) ("digestive effect") or increase in weight (+) ("liquefaction effect") after 2 to 14 hours, expressed as % of the initial values | | | | | | |
|---|---|---|---|---|---|---|---|---|
| Enzyme composition | Conc. g/ml | 2 | 4 | 6 | 8 | 10 | 12 | 14 |
| Krill | 0.01 | + + | + | (+) | − | −(−) | − − | − −(−) |
| | 0.001 | + + | + + | + + | + | +(+) | + | + |
| Control (saliva) | | + +(+) | + + + | + + + | + + + | + + + | + + + | + + +(+) |

Thus according to these results the krill enzyme preparation studied gave a decrease in weight ("digestive effect"). As regards Pankreon ®, preliminary results indicate that this gives merely an increase in weight ("liquefaction effect").

EXAMPLE 11

Effect of Krill Enzymes on the Digestion of Adipose Tissue in the Prescence of Saliva The procedure was the same as in Example 10 except that the substrate was adipose tissue rather than meat.

TABLE 9

| | | Effect on adipose tissue: Decrease in weight (−) ("digestive effect") or increase in weight (+) ("liquefaction effect") after 2 to 14 hours, expressed as % of the initial values | | | | | | |
|---|---|---|---|---|---|---|---|---|
| Enzyme composition | Conc. g/ml | 2 | 4 | 6 | 8 | 10 | 12 | 14 |
| Krill | 0.01 | + | + | (−) | − | − − | − −(−) | − − − |
| | 0.001 | + | + | + | + | + | + | (+) |
| Control (saliva) | | + | + | + | + | + | + | + |

These results are analogous to those of the preceding examples, thus demonstrating that the krill enzymes will be active also in the presence of saliva (that is, in the mouth).

EXAMPLE 12

Effect of Krill Enzymes on Whole Skin from Rat (Keratin, Mucopolysaccharides, Elastin, Adipose Tissue)

Skin biopsies weighing about 50 mg were exposed to krill enzymes in a concentration of 0.01 g/ml. After a period of 24 hours the skin pieces had been digested completely and could no longer be seen in the test tubes.

The same concentration of trypsin resulted after an equal length of time (24 hrs) in an about 50% digestion.

EXAMPLE 13

Digestive Effect of Crude Extracts from Krill and Capelin

This study was carried out in conformity with Examples 4 (for meat) and 7 (for adipose tissue). In the test solutions Pankreon ® and the krill enzymes had been replaced by 1 ml of the extract (thawed) as produced in accordance with Example 1C. and Example 2 respectively. No distilled water was added.

Results (meat): After 8 to 10 hours the crude krill extract was observed to give a substantial decrease in weight ("digestive effect"), according to a pattern similar to though somewhat weaker than that shown in Example 4 (krill enzymes 0.001 g/ml). The crude capelin extract gave a lesser decrease in weight ("digestive effect") than the corresponding krill extract. In the beginning of each experiment a weight increase ("liquefaction") could be observed; this was more pronounced in the capelin extract experiments than in the krill extract experiments.

Results (adipose tissue): In the beginning of each experiment both of the extracts studied gave a weight increase ("liquefaction") during a continuous period which lasted for 10 hours in the case of the krill extract and for 12 hours in the case of the capelin extract. After this period a major decrease in weight ("digestive effect") could be observed in the case of the krill extract, whereas only a weak decrease in weight ("digestive effect") was observable in the case of the capelin extract.

We claim:

1. In a pharmaceutical composition formulated as a tablet, a granulated material, a capsule or a pellet and containing an amount of an enzyme preparation which is effective to promote decomposition of food containing meat or adipose tissue, or meat and adipose tissue, the improvement comprising that the enzyme preparation comprises those watersoluble proteolytic enzymes that (i) can be extracted by an aqueous solvent from an aquatic animal selected from the group consisting of the order Euphausiaceae and of the genus Mallotus, and (ii) have molecular weights, in a non-aggregated form, within the range of 15,000–80,000 daltons.

2. A pharmaceutical composition according to claim 1 wherein the aquatic animal is of the order Euphausiaceae.

3. A pharmaceutical composition according to claim 1 which has been rendered resistant to the action of gastric juice.

4. A pharmaceutical composition according to claim 1 which also contains an additive selected from the group consisting of bile acids, bile salts, gastric juice, small intestinal juice and lipase.

5. In a method for promoting food digestion in gastrointestinal fluids of a terrestrial mammal by oral administration to the said mammal of a composition containing an amount of an enzyme preparation effective to promote the digestion of food containing meat or adipose tissue or meat and adipose tissue, the improvement comprising that said enzyme preparation comprises those water-soluble proteolytic enzymes that (i) are water-soluble in the sense that they can be extracted by an aqueous solvent from an aquatic animal selected from the order Euphausiaceae or the genus Mallotus, and (ii) have molecular weights, in a non-aggregated state, within the range of 15,000–80,000 daltons.

6. A method according to claim 5 wherein the aquatic animal is of the order Euphausiaceae.

* * * * *